US005726060A

United States Patent [19]
Bridges

[11] Patent Number: 5,726,060
[45] Date of Patent: Mar. 10, 1998

[54] METHOD FOR CULTURING MAMMALIAN RESPIRATORY EPITHELIAL CELLS

[76] Inventor: Michael Anthony Bridges, 3435 West 37th Ave., Vancouver, Canada, V6N 2V5

[21] Appl. No.: 421,817

[22] Filed: Apr. 13, 1995

Related U.S. Application Data

[63] Continuation-in-part of Ser. No. 081,626, Jun. 23, 1993, abandoned, which is a continuation-in-part of Ser. No. 760,954, Sep. 17, 1991, abandoned.

[51] Int. Cl.$^6$ .............................. C12N 5/02; C12N 5/06
[52] U.S. Cl. .................... 435/395; 435/383; 435/384; 435/387; 435/391; 435/392
[58] Field of Search ............... 435/240.2, 240.21, 435/240.23, 240.241, 240.243, 240.3, 297.1, 366, 350, 351, 352, 363, 371, 383, 384, 385, 387, 391, 395

[56] References Cited

U.S. PATENT DOCUMENTS

| | | | |
|---|---|---|---|
| 4,446,234 | 5/1984 | Russo et al. | 435/29 |
| 4,963,490 | 10/1990 | Churchouse et al. | 435/240.241 |
| 5,190,878 | 3/1993 | Wilhelm | 435/297.2 |

OTHER PUBLICATIONS

Reen Wu et al., "Growth and Differentiation of Human Nasal Epithelial Cells in Culture", (1985) Am. Rev. Respir. Dis. 132: 311–320.

J.R. Yankaskas et al., "Culture of Human Nasal Epithelial Cells on Collagen Matrix Supports: A Comparison of Bioelectric Properties of Normal and Cystic Fibrosis Epithelia", (1985) Am. Rev. Respir. Dis. 132: 1281–1287.

J.F. Lechner and M.A. LaVeck, "A Serum–free Method for Culturing Normal Human Bronchial Epithelial Cells at Clonal Density", (1985) J. Tiss. Cult. Meth. 9: 43–48.

J. Rutland and P.J. Cole, "Non-invasive Sampling of Nasal Cilia for Measurement of Beat Frequency and Study of Ultrastructure", (1980) Lancet 2: 564–565.

Bridges et al., "Culture of CF and Control Nasal Epithelial Cells Harvested by a Minimally–invasive Brushing Procedure", Poster Presentation to the 10th International Cystic Fibrosis Congress, Sydney, Australia (5–9 Mar., 1988).

Bridges et al., "Development of Cystic Fibrosis (CF) and Control Nasal Epithelial Cell Culture, Utilizing Cells Harvested by a Cell Brushing Technique", Poster Presentation to the 1988 North American CF Conference, Orlando, Florida (28 Sep.–1 Oct., 1988).

B.R. Wilson, D.C. Walker, R.A. Harris, A.G.F. Davidson and M.A. Bridges, "Human Nasal Epithelial Multicellular Spheriods (HNEMS)", Poster Presentation to Univ. of British Columbia Health Sciences Research Symposium, Vancouver, Canada (Oct. 1988).

M.A. Bridges, B.R. Wilson, R.A. Harris, D.C. Walker and A.G.F. Davidson, "Cultured Human Nasal Epithelial Multicellular Spheriods (HNEMS): Non–transformed Hollow Organoids Displaying Morphological and Functional Polarity", F.A.S.E.B. Meetings, New Orleans, LA. (Mar. 1989).

M.A. Bridges, A.G.F. Davidson, B.R. Wilson, R.M. Balen and E.R. Roth, "Culture of Human Airway Epithelial Cells: Application to Cystic Fibrosis Studies", Pharmaceutical Sciences Research Day Conference, UBC, Vancouver, British Columbia (May 1989).

M.A. Bridges, B.R. Wilson, R.A. Harris, D.C. Walker and A.G.F. Davidson, "Human Nasal Epithelial Multicellular Spheroids (HNEMS): A Transporting, Cyst–like Cultured Airway Tissue Model", Pharmaceutical Sciences Research Day Conference, UBC, Vancouver, British Columbia (May 1989).

M.A. Bridges, B.R. Wilson, R.A. Harris, D.C. Walker and A.G.F. Davidson, "Human Nasal Epithelial Multicellular Spheroids (HNEMS): A Transporting, Cyst–like Cultured Airway Tissue Model", 1989 North American Cystic Fibrosis Conference, Tarpon Springs, Florida (Oct. 1989).

Bridges et al., "Nasal Mucusol Brushing: Investigation of the Basic Defect in Cystic Fibrosis by the Use of Nasal Epithelial Brushing", (1988) B.C. Pharmacists vol. 1 (#3), pp. 17–18.

R. Grygorczyk, L. Schlichter, M.A. Bridges and A.G.F. Davidson, "Ion Channels in Human Brushed Nasal Epithelial Cells", Poster Presentation to 4th North American Cystic Fibrosis Conference, Arlington, VA. (Oct. 1990).

(List continued on next page.)

*Primary Examiner*—Jean C. Witz
*Attorney, Agent, or Firm*—Oyen Wiggs Green & Mutala

[57] ABSTRACT

A method of culturing non-transformed mammalian respiratory epithelial cells in vitro. The method includes the steps of harvesting the epithelial cells from the respiratory tract of a mammalian donor; suspending the epithelial cells in a fluid culture medium to form a cell suspension; introducing the cell suspension into a first reservoir in communication with an adherence substrate; introducing additional fluid culture medium into a second reservoir separated from the first reservoir by a fluid permeable baffle; incubating the cells under conditions suitable for promoting epithelial cell growth for a period of at least 72 hours; and changing the fluid culture medium within the second reservoir during the incubation period at intervals of approximately 24–72 hours without disturbing the epithelial cells within the first reservoir. Preferably, the epithelial cells are harvested from the nasal mucosa of a human donor using a minimally-invasive brushing technique. A novel culture dish suitable for carrying out the method is also described. The culture dish includes first and second reservoirs for holding fluid culture medium; a fluid permeable first baffle separating the first and second reservoirs; an adherence substrate in communication with at least the first reservoir; and an open-ended second baffle positionable within the first reservoir between the first baffle and the adherence substrate for restricting the circulation of the fluid culture medium within the first reservoir.

20 Claims, 4 Drawing Sheets

OTHER PUBLICATIONS

M.A. Bridges, A.G.F. Davidson and D.C. Walker, "Culture of Cystic Fibrosis and Control Nasal Epithelial Cells Harvested by a Brushing Procedure", In Vitro 27A: 684–686 (1991).

R. Grygorszyk and M.A. Bridges, "Whole–Cell Chloride Conductances in Cultured Brushed Human Nasal Epithelial Cells", Can. J. Physiol. Pharmacol. 70: 1134–1141 (1992).

Steven G. Kelsen et al., "A Technique to Harvest Viable Tracheobronchial Epithelial Cells from Living Human Donors", Am. J. Respir. Cell Mol. Biol. vol. 7, pp. 66–72 (1992).

M.A. Bridges et al., "Cystic Fibrosis Nasal Epithelial Cell Cultures." Poster Presentation to Research Week B.C. Children's Hospital Research Division, Vancouver, British Columbia (Oct. 1989).

METHOD FOR CULTURING MAMMALIAN RESPIRATORY EPITHELIAL CELLS

This is a continuation-in-part of application Ser. No. 08/081,626 filed Jun. 23, 1993, now abandoned, which was a continuation-in-part of application Ser. No. 07/760,954 filed Sep. 17, 1991, now abandoned.

FIELD OF THE INVENTION

This application relates to a method of culturing respiratory epithelial cells in vitro. More particularly, this application pertains to a method of culturing epithelial cells harvested from the nasal mucosa of a human donor using a minimally-invasive brushing technique.

BACKGROUND OF THE INVENTION

Many diseases are known to affect the human respiratory tract. For example, cystic fibrosis, which is the most common lethal inherited disease affecting the Caucasian population, has been linked to the production of a defective protein which appears to affect electrolyte transport across respiratory epithelial tissues. However, elucidation of the molecular basis of the cystic fibrosis transport defect has been hampered by the lack of suitable epithelial tissue available for study. Until now, the most readily obtainable cystic fibrosis epithelial tissue has been nasal mucosa acquired as a by-product of polypectomy or rhinoplasty. However, such specimens have been in very limited supply and often show reduced viability due to anaesthesia, trauma or infection. Moreover, increased use of intra-nasal steroid treatments in recent years has further reduced the availability of polypectomy tissue.

Researchers have consequently investigated other techniques for harvesting respiratory epithelial cells, such as nasal brushing or scraping. Nasal brushing involves the manual insertion of a cytology brush into the nasal passages of a living donor, such as a cystic fibrosis patient. Epithelial cells are collected by reciprocal and rotary movement of the brush on the donor's nasal mucosa. This technique is minimally-invasive and is well tolerated by adult and paediatric donors.

Previous attempts to culture brushed or scraped human nasal epithelial (BHNE) cells in vitro have not been successful. The primary difficulty facing tissue culturists has been the failure of BHNE cells to adhere to in vitro substrates for significant periods of time. Even when they do initially adhere, BHNE cells will usually peel off the chosen substrate after several days without flattening and replicating. Accordingly, such cells cannot be reliably used for biochemical and electrophysiological experiments or diagnostic testing, nor can they be amplified by serial subcultivation.

In an attempt to increase cell seeding efficiencies the applicant has investigated various protocols for enhancing BHNE cell adherence. For example, a wide variety of substrates have been investigated for culturing BHNE cells in vitro, including substrates coated with laminin, lectin, lipoteichoic acid, fibronectin and type I or type IV collagen. Using standard plating, washing and feeding procedures, most of the aforesaid substrates have demonstrated only minimal cell adherence.

The subjection of BHNE cells to a period of recovery after harvesting and prior to plating on the in vitro substrate also has no beneficial effect on BHNE cell seeding efficiencies. Other approaches for enhancing cell adherence have included treating the harvested cells with enzymes to break down the mucus and DNA gel typically entrapping the harvested BHNE cells and preventing cellular contact with the substrate surface. Another proposed protocol involves treating the BHNE cells with chemical activators in order to expose membrane adherence sites. However, such techniques have met with only limited success and often result in pharmacological side effects and abnormal cell morphology which renders the cultured BHNE cells unsuitable for scientific study.

Accordingly, the need has arisen for a readily reproducible method for culturing BHNE cells in vitro which has a high cell adherence and seeding efficiency.

SUMMARY OF THE INVENTION

In accordance with the invention, a method of culturing non-transformed mammalian respiratory epithelial cells in vitro is disclosed. The method includes the steps of harvesting the epithelial cells from the respiratory tract of a mammalian donor; suspending the epithelial cells in a fluid culture medium to form a cell suspension; introducing the cell suspension into a first reservoir having a bottom surface comprising an adherence substrate; introducing additional fluid culture medium into a second reservoir separated from the first reservoir by a fluid permeable baffle; incubating the cells under conditions suitable for promoting epithelial cell growth for a period of at least 72 hours; and changing the fluid culture medium within the second reservoir during the incubation period at intervals of approximately 24–72 hours without disturbing the epithelial cells within the first reservoir.

Preferably the incubation step is continued until the epithelial cells form a confluent layer on the adherence substrate or until greater than about 25% of the epithelial cells adhere, flatten and begin to replicate on the adherence substrate.

Preferably, the epithelial cells are harvested by brushing or scraping of the respiratory tract mucosa of a donor organism.

Some of the epithelial cells within the cell suspension are present as aggregates of initially non-adherent cells (the cells are harvested as aggregates and maintain their cell/cell junctional contacts in solution). Preferably the incubation step is continued until the majority of such initially non-adherent cells adhere, flatten and begin to replicate on the adherence substrate.

In one embodiment of the invention, the baffle separating the first and second reservoirs may comprise the adherence substrate. In this case, the adherence substrate is fluid permeable and may include an upper surface exposed to the first reservoir and a lower surface exposed to the second reservoir.

In an alternative embodiment of the invention, the adherence substrate may be fluid impermeable, such as a glass coverslip coated with an adherence surface. In this embodiment the fluid impermeable substrate covers only a portion of the fluid permeable baffle to allow continued fluid communication between the first and second reservoirs.

A culture dish is also disclosed for culturing cells in vitro. The culture dish includes first and second reservoirs for holding fluid culture medium; a fluid permeable first baffle separating the first and second reservoirs; an adherence substrate in communication with at least the first reservoir; and an open-ended second baffle positionable within the first reservoir between the first baffle and the adherence substrate for restricting the circulation of the fluid culture medium within the first reservoir.

BRIEF DESCRIPTION OF THE DRAWINGS

In drawings which illustrate embodiments of the invention, but which should not be construed as restricting the spirit or scope of the invention in any way.

DETAILED DESCRIPTION OF THE PREFERRED EMBODIMENT

This application relates to a method of culturing respiratory epithelial cells in vitro. The method is particularly suited to culturing of epithelial cells harvested from the nasal mucosa of a human donor using a minimally-invasive brushing technique. The cultured cells may provide a ready source of non-transformed epithelial tissue for various applications, such as morphological, histochemical, molecular biological, biochemical and electrophysiological experiments, and may be amplified in number by serial subcultivation techniques. For example, the brushed human nasal epithelial (BHNE) cells cultured in accordance with the method may be used to study the patho-physiology of human diseases affecting the respiratory tract, such as cystic fibrosis.

Figure 1:
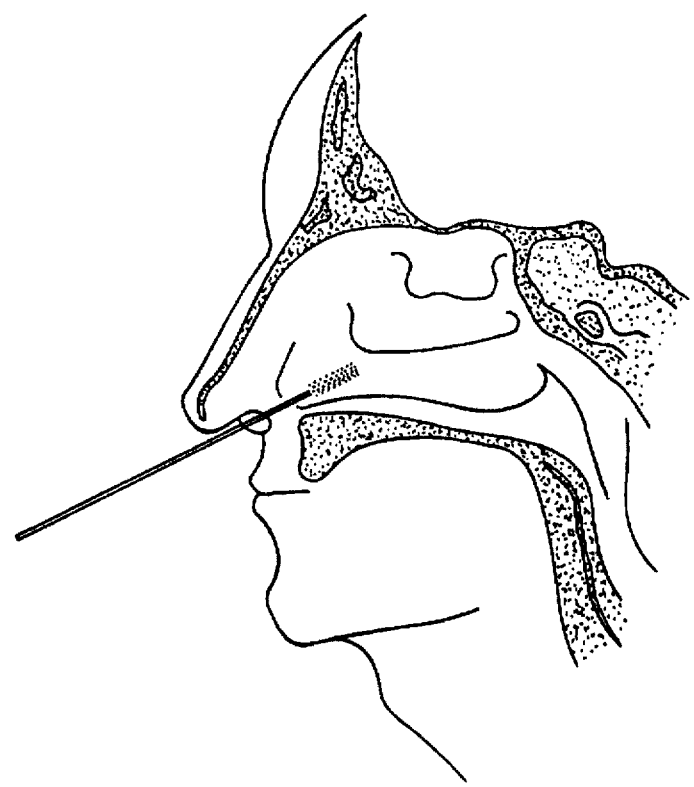
FIG. 1 is a pictorial section showing the preferred method of harvesting epithelial cells by inserting a cytology brush into a nasal passage of a human donor and passing the brush over the mucosa of the inferior turbinate and adjacent lateral nasal wall.

The BHNE cells are preferably harvested from a human donor, such as a cystic fibrosis patient, by nasal brushing. Nasal brushing is a simple, non-surgical procedure, well tolerated by patients and requiring no anaesthesia. As shown in FIG. 1, nasal brushing involves the insertion of a sterile cytology brush into the nasal passages of the donor under direct visualization using a headlamp. A suitable sterile cytology brush is available from Wilson-Cook Medical Inc. of Winston-Salem, N.C. (#BCB-5-30-3-UBC). The cytology brush is inserted (through a nasal speculum) along the tip of the inferior turbinate and the adjacent lateral nasal wall of the donor, and epithelial cells are collected by a reciprocal and rotary movement of the brush on the nasal mucosa. Although minor irritation, reflex lachrymation or sneezing may occur with the brushing procedure, these sensations are rarely described as painful and only occasionally are trace quantities of erythrocytes harvested with the brushed epithelial cells. However, in order to avoid overt pain and bleeding, the operator should only brush the lateral nasal wall since the medial wall is typically highly vascularized and sensitive.

Depending upon the donor and the skill of the operator, between 0.01–1.0 million viable BHNE cells can be harvested from each bilateral brushing of a donor's nasal mucosa and used directly for analytical studies or for culture experiments. The harvested cells from one nasal brushing are suspended in a fluid collection medium. Prior to re-application to the donor's nasal mucosa for the contralateral brushing, the brush is washed in sterile phosphate buffered saline in order to avoid exposing the donor to potentially harmful constituents of the collection medium, such as dyes.

According to the method of the present invention, epithelial material adhering to the nasal brush is removed by brisk agitation in a fluid collection medium, such as 3.0 ml sterile Ham's F12 medium, which is available from Sigma Chemical Co. of St. Louis, Mo. Preferably the epithelial material harvested from both of the bilateral brushings is pooled in the fluid collection medium to maximize BHNE cell concentrations. The pooled BHNE cells are then treated with epithelial cell activating and adherence factors, such as contained in 10% (vol/vol) fetal bovine serum, pelleted by centrifugation (150× g for 6 minutes), and resuspended in a fluid plating medium, such as 0.3 ml supplemented Ham's F12 medium. The Ham's F12 medium is preferably supplemented with the following hormone factors in accordance with the protocol described by Yankaskas et al (Am. Rev. Respir. Dis. 132:1281–1287; 1985 and personal communication with the inventor): 2 ug/ml insulin, 100 nM hydrocortisone, 3 nM triiodothyronine, 4 ug/ml endothelial cell growth supplement, 12.5 ng/ml epidermal growth factor and 10 ng/ml cholera toxin. In an alternative embodiment, a higher concentration of triiodothyronine (31 nM) may be used to further promote cell growth.

After the BHNE cells have been treated as aforesaid, they are immediately plated onto an in vitro substrate. It does not appear to be beneficial to subject the BHNE cells to a recovery period following the trauma of harvesting and prior to plating. Indeed, best results are achieved when the time period from harvesting to plating is minimized (i.e. less than 20 minutes).

Preferably the harvested cells should not be enzymatically treated (such as with proteases or DNases) prior to plating on the in vitro substrate. Conventionally epithelial cells harvested from the respiratory mucosa (such as by excision of nasal polyps) are enzymatically treated, primarily in order to separate the epithelial cells from the remainder of the excised tissue block. Enzymatic digestion of excised tissue is typically followed by macrofiltration and centrifugation to yield a cell pellet.

Enzymatic treatment of respiratory epithelial tissue obtained by excision or nasal brushing techniques was also previously considered important to breakdown the mucus and DNA gel typically entrapping epithelial cells. The mucus is derived from goblet cells which line the mucosa and which release mucus in response to manual or chemical stimulation. The DNA is released from cells traumatized during the manual or chemical harvesting procedure. The primary purpose of enzymatic pre-treatment is to increase the opportunity for epithelial cell contact with the in vitro substrate and to maximally expose epithelial cell membrane adherence sites by dissociating multi-cellular tissue clusters into smaller groupings. However, the inventor has discovered that enzymatic pre-treatment of BHNE cells is neither necessary nor desirable. Rather, as discussed below, if the BHNE cells are left in an undisturbed state for a sufficient period of time (i.e at least 3 days and preferably 7–10 days), they will eventually become dissociated from the surrounding mucus/DNA gel and adhere, flatten and replicate on the in vitro substrate.

The terms "undisturbed" and "without disturbing" as used throughout this application mean that the epithelial cells are not washed, rinsed or otherwise removed from the in vitro culture dish during the incubation step. Rather, the plated cells are maintained in a substantially non-agitated state within a "first reservoir" of the culture dish and are fed periodically by changing the fluid culture medium in a "second reservoir" of the culture dish, which is separated from the first reservoir by a permeable membrane. The membrane essentially functions as a baffle which ensures that the cells within the first reservoir are not significantly disturbed when the culture medium is changed. As discussed further below, this procedure enables the initially non-adherent epithelial cells to eventually adhere to an in vitro substrate in communication with the first reservoir, resulting in markedly enhanced seeding efficiencies.

Of course, the plated BHNE cells introduced into the first reservoir may be agitated to a minor extent when the culture dish is manually handled. This minor degree of disturbance is tolerable, provided that the cells are not rinsed, washed or removed from the first reservoir during the incubation period.

Figure 2:
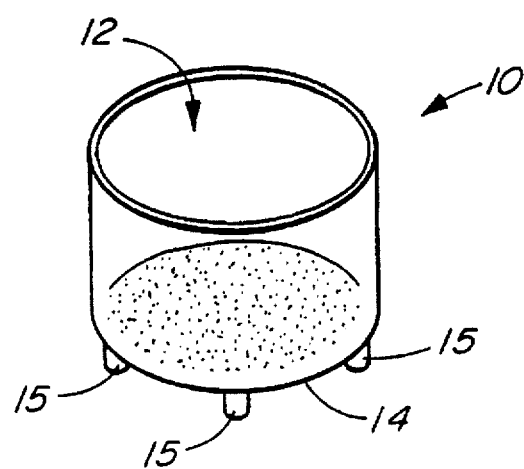
FIG. 2 is an enlarged, isometric view of a culture dish insert which serves as a preferred in vitro substrate.
Figure 3:
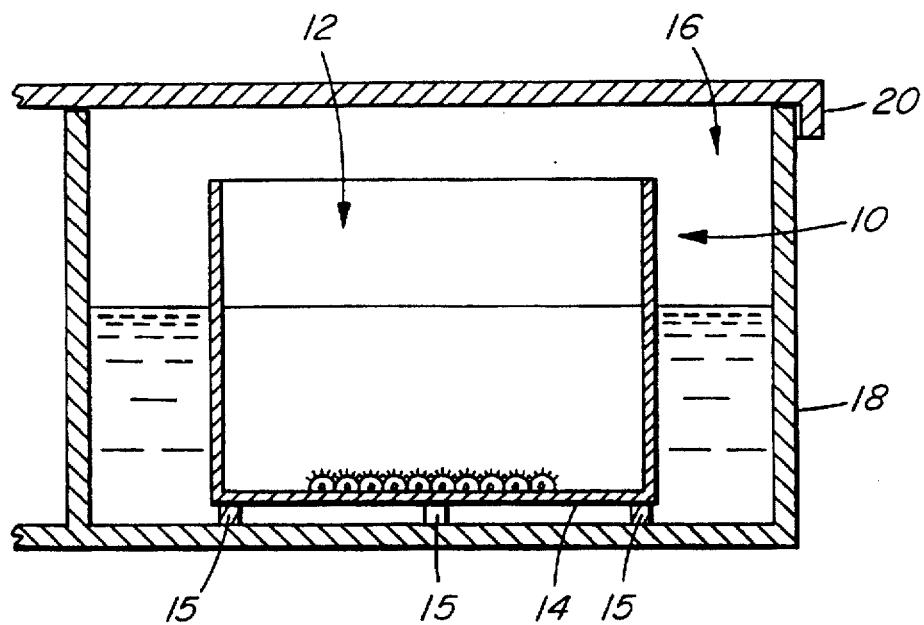
FIG. 3 is an enlarged, fragmented, side elevational view of the insert of FIG. 2 positioned within a culture dish.

One preferred in vitro substrate is collagen derived from bovine chorionic membrane tissue. A suitable collagen substrate is sold under the trade-mark CELLAGEN™ and is available from ICN Biomedical Inc. of Cleveland, Ohio (CD-24; ICD 152316) As illustrated in FIG. 2, the CELLAGEN™ substrate comprises a culture dish insert 10 having a reservoir or well 12 for receiving culture medium and an adherence substrate 14 comprising collagen derived from bovine chorionic membrane tissue. Adherence substrate 14 is fluid permeable. As shown in FIG. 3, insert 10 is positionable into one reservoir or well 16 of a sterile, multi-welled microtiter dish 18 having a lid 20. Insert 10 includes a plurality of foot supports 15 spaced around its periphery for elevating adherence substrate 14 above the bottom of dish 18.

The entire BHNE inoculum derived from a single donor is introduced into insert reservoir 12. Best results have been achieved with inserts 10 having a relatively small diameter (14 mm), probably due to increased cell density within reservoir 12. Small diameter inserts 10 also restrict fluid circulation within reservoir 12 which helps maintain the cell inoculum in an undisturbed state. Insert 10 is then placed into a reservoir 16 of dish 18 and fluid culture medium is added to reservoir 16 until it is roughly even with the level of culture medium within insert reservoir 12 (FIG. 3). The fluid culture medium permeates across adherence substrate 14 until a steady-state is reached (i.e the volume of fluid in reservoirs 12, 16 is level). Of course, fluid culture medium, cellular waste products, nutrients, and the like continues to diffuse across adherence substrate 14.

After all of the CELLAGEN™ inserts 10 have been inoculated and placed in a respective culture dish reservoir 16 as described above, lid 20 is secured to dish 18 and the culture dish assembly is incubated at 37° C. and 5% $CO_2$. A key feature of the present method is that the BHNE cells are left in insert reservoir 12 in contact or potential contact with adherence substrate 14 in an undisturbed state for a protracted period of time (i.e. at least 3 days following plating). As shown in FIG. 2, adherence substrate 14 is supported above the bottom of dish 18 by foot supports 15. Thus, fluid permeable adherence substrate 14 is exposed to culture medium introduced into dish reservoir 16 in addition to the culture medium within insert reservoir 12. During the incubation stage the culture medium within dish reservoir 16 is periodically aspirated and replenished with fresh medium. Thus a partial medium change can be easily effected without significantly disturbing adherent and non-adherent BHNE cells introduced into insert reservoir 12.

The above-described procedure is contrary to conventional tissue culture techniques used to grow primary (non-transformed) mammalian epithelial cells. For most of these cell types which can be successfully cultured, seeded cells adhere to the in vitro substrate and begin to flatten in a matter of a few hours. Therefore, tissue culturists generally remove the seeded non-adherent material from the plate after 1–3 days in culture (*Culture of Animal Cells: A Manual of Basic Technique* by R. Ian Freshney (Allan R. Liss, Inc.: 1987)). The primary rationale for this procedure is that non-transformed mammalian epithelial cells are anchorage-dependent and they die very quickly (typically within 2–3 days in culture) if they cannot adhere to a substrate. When they die, such cells typically release cellular products which are toxic or inhibitory to adherent cells, such as proteases, nucleases, cytokines or lysosomal enzymes. Thus, ordinarily it is advisable to remove non-adherent cells after 1–3 days in culture by extensively rinsing the in vitro substrate with medium and aspirating the non-adherent cells, rather than leaving such cells in the culture dish in contact or potential contact with adherent cells.

Figure 4:
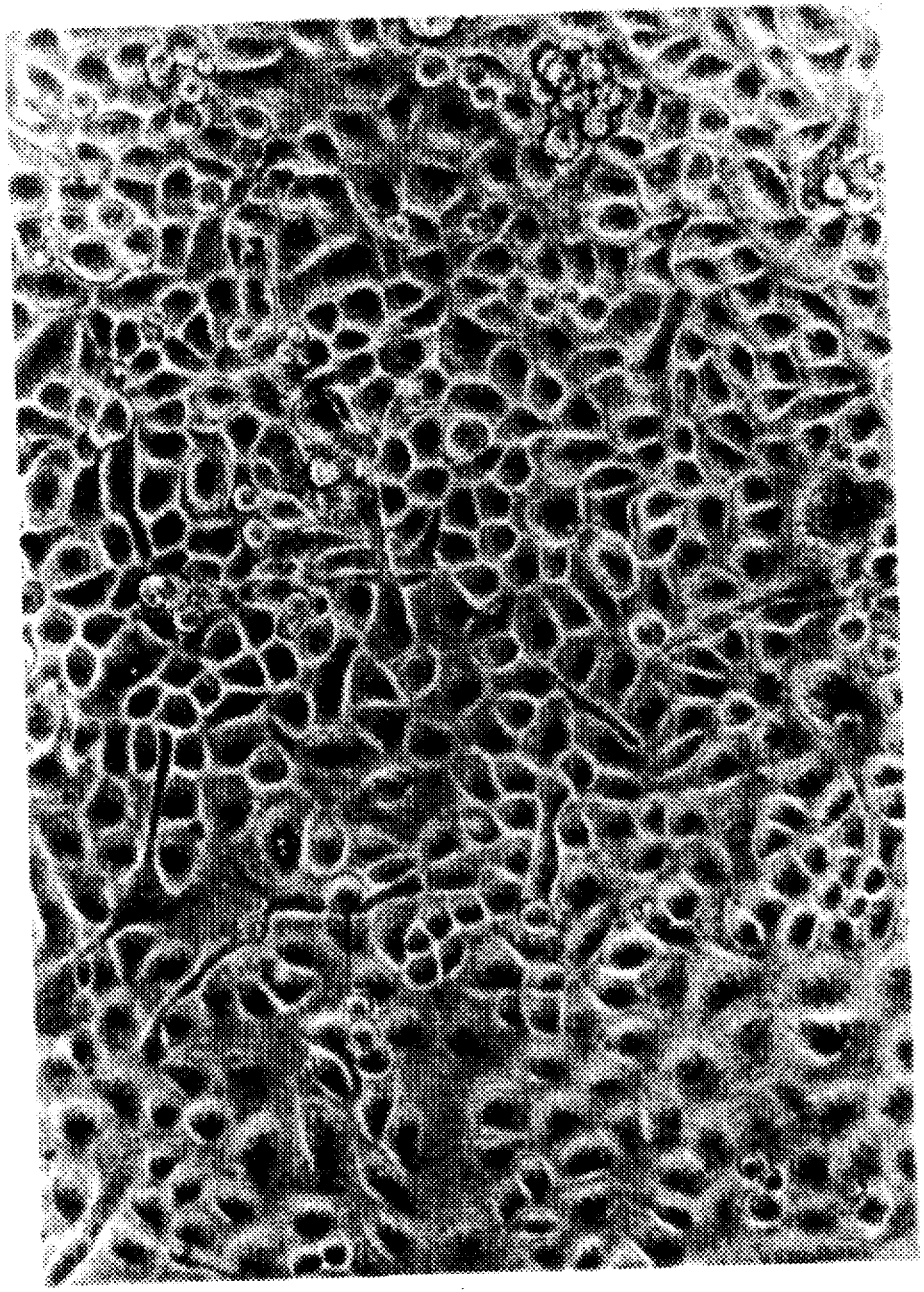
FIG. 4 is phase contrast micrograph of a confluent layer of epithelial cells derived from brushed tissue harvested from the nasal mucosa of a human donor and cultured in accordance with the invention.

It appears that BHNE cells do not demonstrate the same anchorage-dependent characteristics as other mammalian epithelial cells. In this respect BHNE cells appear to differ from enzyme-dissociated nasal epithelial cells harvested by excision from the same area of the nasal mucosa. Although the BHNE cells are still primary and non-transformed, they appear to have the ability to survive in an non-anchored state due to their continued association with neighbouring cells in tissue-like structures, thereby mimicking the in vivo situation. In particular, the cell/cell and cell/substrate junctional contacts are maintained. Some of these tissue-like structures can seed to form adherent cell layers on adherence substrate 14, as shown in FIG. 4.

Other BHNE cells appear to form hollow spheroidal aggregates which continue to transport salt and fluid. Such spheroidal aggregates range between 50–600 um in diameter with walls which are a single cell thick (the apical membrane surfaces face outward and the basolateral membrane surfaces face the fluid-filled lumen of the spheres). Some spheres display cilia on their outer, apical membrane surfaces which beat synchronously, suggesting the spheres behave as a functional syncytium. If left in an undisturbed state in insert reservoir 12 for a sufficient period of time (preferably 7–10 days), the spheroidal aggregates will eventually adhere to adherence substrate 14 and flatten. At least some of the epithelial cells comprising the aggregates then typically begin to replicate on adherence substrate 14, thus enhancing cell seeding efficiency.

As discussed above, in order to achieve high (i.e. 25–50% or more) seeding efficiencies, it is necessary to maintain the BHNE cells in contact with adherence substrate 14 in an undisturbed state for a protracted period of time (i.e. at least 3 days and preferably 7–10 days) following plating, while periodically replenishing the culture medium in dish reservoir 16. One preferred initial culture medium is Ham's F12 medium supplemented as described above. After approximately 2–3 days of incubation it is preferable to introduce a fluid culture medium supplement into reservoir 16, such as modified LHC9 medium. Modified LHC9 medium is based on MCDB 151 medium available from Sigma Chemical Co. and is prepared according to the recipe described by Lechner and LaVeck (J. Tiss. Cult. Meth. 9: 43 [1985]) with the following modification: substitute 4 ug/ml endothelial cell growth supplement for bovine pituitary extract and 10 ng/ml cholera toxin for epinephrine. The modified LHC9 medium is primarily designed to stimulate cell proliferation and inhibit cell differentiation so that the BHNE cells retain replicative capacity for a longer period of time, thereby enhancing cell numbers in primary culture and enabling successful subcultivation.

Another fluid collection medium that has proven effective is bronchial epithelial basal medium (BEBM) which is available from Clonetics Corp. of San Diego, Calif. When used as a fluid culture medium BEBM is supplemented with various hormones and growth factors similar to those contained in the LHC9 medium referred to above. The supplemented BEBM is also available from Clonetics Corp. and is referred to as bronchial epithelial growth medium (BEGM). The hormone and growth factor supplements contained in BEGM are as follows: 0.11 mM CaCl2; 0.5 ug/ml hydrocortisone; 0.51 ng/ml EGF; 64 ug/ml BPE; 5 ug/ml insulin; 10 ug/ml transferrin; 0.5 ug/ml epinephrine; 6.5 ng/ml triiodothyronine; and 0.1 ng/ml retinoic acid. The BEBM and BEGM mediums have a base calcium concentration 110 uM, but may be spiked with additional calcium depending upon the degree of cellular proliferation and differentiation required. Calcium concentrations in the range of 110 uM–400 uM are preferable for most purposes. As should be apparent to someone skilled in the art, reduced calcium concentration in the fluid culture medium enhances epithelial cell proliferation in vitro.

Feeding of the BHNE cells by introduction of fresh modified LHC9 medium or BEGM into dish reservoir 16 should take place approximately every 2–3 days. After about 7–10 days in culture, up to 50% of the initially non-adherent BHNE cell clusters will seed onto adherence substrate 14, thereby producing a confluent cellular layer (FIG. 4). Seeding efficiency increases in direct proportion to the number of initially non-adherent BHNE cells which are permitted to remain in insert reservoir 12 in an undisturbed state for longer than 3 days. Since nasal brushing usually yields a small amount of starting cells for plating purposes, a relatively high seeding efficiency is essential in order to achieve useful BHNE cultures. As discussed above, the initial inoculum resulting from nasal brushing typically comprises considerably less than one million BHNE cells. By way of comparison, cells harvested from excised tissue can yield two to seven million epithelial cells or more for initial plating purposes.

BHNE cells cultured on CELLAGEN™ discs as aforesaid may be readily passaged onto plastic surfaces for serial subcultivation, resulting in a 10 to 25-fold amplification in cultured cell numbers. The passaging protocol found to be effective is as follows: when BHNE cultures are 80–90% confluent, adherent cells are removed from the collagen substrate by trypsinization for 5–20 minutes at 25°, using a HEPES-buffered saline solution containing 0.02% (w/v) trypsin, 0.02% (w/v) EGTA, 1.0% (w/v) polyvinylpyrrolidone (Lechner and LaVeck, supra). Dissociated cells are then treated with 10% (v/v) fetal bovine serum (FBS), pelleted by centrifugation (150× g for 6 min), washed in Ham's F12 or BEBM medium containing 10% (v/v) FBS and recentrifuged. The cell pellet is then resuspended in Ham's F12 medium as supplemented above or BEGM and plated onto plastic tissue cultureware (Corning) and incubated at 37° C. and 5% $CO_2$ for 24–48 hours. Cell cultures are washed and fed with modified LHC9 medium or BEGM as described above. Using this protocol, up to two passages could be performed, amplifying the number of cultured BHNE cells available for further study.

By way of example, in one study conducted by the applicant 22 BHNE cultures were observed for a period of 14 days following plating. The BHNE cells were harvested and incubated in an undisturbed state as described above utilizing BEBM as the initial fluid collection medium and BEGM as the fluid culture medium. The plated BHNE cells, cell clusters and spheroids were observed using an inverted phase contrast microscope at regular intervals. The time required for each cell culture to reach confluence was recorded. Freshney (supra at p. 363) defines "confluent" as meaning "where all the cell are in contact all round their periphery with other cells, and no available substrate is left uncovered." In this study, no BHNE cells, cell clusters or spheroids were observed to have adhered to the adherence substrate 14 prior to 72 hours in culture. All of the 22 cultures eventually reached confluence during the culture period: 55% of the cultures became confluent within 6–9 days in culture and 45% of the cultures became confluent within 10–14 days in culture.

By way of further example, Tables 1 and 2 below summarize the results of a further time course study relating to the culture of BHNE cells in vitro in accordance with the applicant's method. Table 1 relates to a study involving 7 BHNE cultures observed over an 11 day period. The BHNE cells were harvested and incubated in an undisturbed state as described above utilizing BEBM as the initial fluid collection medium and BEGM as the fluid culture medium. The cells were grown under standard calcium conditions (i.e. 110 uM $Ca^{2+}$). The plated BHNE cells, cell clusters and spheroids were observed using an inverted phase contrast microscope at regular intervals and the percent confluence was recorded.

TABLE 1

| Time period   | Percent Confluence |
|---------------|--------------------|
| Culture Day 3 | Nil                |
| Culture Day 5 | 4.3% ± 0.7%        |
| Culture Day 7 | 18.9% ± 2.6%       |
| Culture Day 9 | 55.7% ± 3.8%       |
| Culture Day 11| 84.3% ± 2.1%       |

Table 2 relates to a study involving 4 BHNE cultures observed over an 11 day period. The BHNE cells were harvested and incubated in an undisturbed state as described above utilizing BEBM as the initial fluid collection medium and BEGM as the fluid culture medium. The cells were grown under elevated calcium conditions (i.e. 400 uM $Ca^{2+}$). The plated BHNE cells, cell clusters and spheroids were observed using a microscope at regular intervals and the percent confluence was recorded.

TABLE 2

| Time period   | Percent Confluence |
|---------------|--------------------|
| Culture Day 3 | Nil                |
| Culture Day 5 | Nil                |
| Culture Day 7 | 12.5% ± 5.4%       |
| Culture Day 9 | 24.8% ± 7.3%       |
| Culture Day 11| 55.3% ± 10.1%      |

The above studies demonstrate in quantitative terms the importance of not removing non-adherent material from the culture dish 18 at the first or second medium change (typically 1–3 days in culture). If in the above studies the non-adherent BHNE cells had been rinsed and removed from the culture dish 18 in accordance with conventional procedures, all of the cultures would have failed entirely or yielded very low cell seeding efficiencies. As discussed above, it appears that BHNE cells harvested by brushing or scraping of the respiratory tract mucosa are not anchorage dependent in the same manner as cells harvested by other means and are capable of remaining viable in fluid suspension for extended periods of time. If left in an undisturbed state for extended periods, the non-adherent clusters of BHNE cells in solution will eventually dissociate from any mucus and DNA gels which envelop them and adhere to the substrate 14. Contrary to conventional thinking, it appears that such non-adherent BHNE cells do not release toxic or inhibitory substances adversely affecting the viability of adherent cells.

Figure 5:
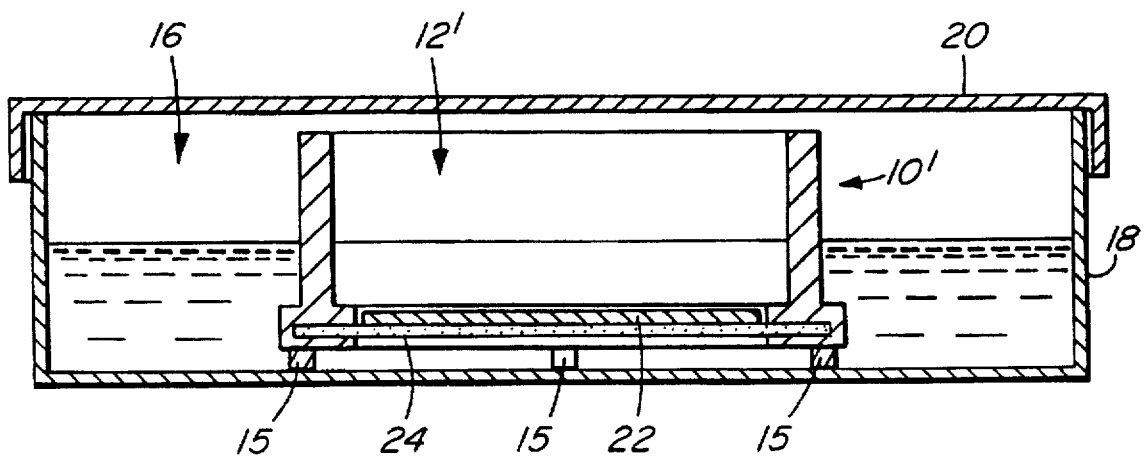
FIG. 5 is a sectional view of an alternative culture dish insert.

FIG. 5 illustrates an alternative culture dish insert $10^1$ for culturing BHNE cells on an impermeable substrate. As in the FIG. 3 embodiment, insert $10^1$ is positionable within one reservoir 16 of a sterile culture dish 18 having a lid 20.

Insert $10^1$ defines an open-topped reservoir $12^1$ for holding the harvested BHNE cells suspended in fluid culture medium. The bottom of reservoir $12^1$ is formed by a fluid impermeable substrate 22 supported by a fluid permeable membrane 24. Impermeable substrate 22 may comprise a glass coverslip coated with an adherence surface, such as poly-L-lysine or fetal bovine serum (FBS). As in the FIG. 3 embodiment, insert $10^1$ also includes a plurality of foot supports 15 for elevating impermeable substrate 22 and membrane 24 above the bottom of dish 18. The bronchial epithelium growth medium (BEGM) cell culture medium referred to above has proven effective for culturing BHNE cells on impermeable substrates 22, such as poly-L-lysine or FBS coated glass coverslips.

With reference to FIG. 5, the BHNE inoculum derived from a donor is suspended in a fluid culture medium (such as BEGM having a calcium concentration of 110 uM), and introduced into reservoir $12^1$ of insert $10^1$. In accordance with the applicant's culture method, the BHNE cells are left in reservoir $12^1$ in an undisturbed state for a protracted period of time (i.e. greater than 3 days) in contact or potential contact with the adherence surface coated on impermeable substrate 22. During this incubation period the culture medium within dish reservoir 16 is aspirated and replenished with fresh medium approximately every 48-72 hours. The fresh medium permeates across membrane 24 (in those regions not covered by impermeable substrate 22) and into reservoir $12^1$ to sustain the adherence and replication of the plated BHNE cells. As explained above, a significant advantage of this procedure is that the culture medium can be periodically replenished without disturbing the weakly adherent and non-adherent BHNE cells within reservoir $12^1$.

The applicant's method for culturing epithelial cells on impermeable substrates 22 is contrary to conventional cell culture protocols. As explained above, ordinarily non-adherent material is removed after approximately 1-3 days in culture. The remaining cells adhering to the in vitro substrate are thoroughly rinsed with fresh culture medium. These procedures are extremely disruptive and result in the removal of viable BHNE cells and detachment of weakly adhering cells from the substrate. The applicant postulates that premature disturbance of the plated BHNE cells in this manner is one of the primary causes of low seeding efficiencies using conventional culture methods.

BHNE cells cultured on impermeable substrates 22, such as glass coverslips covered with poly-L-lysine, may exhibit different morphological characteristics than cells cultured on permeable substrates such as collagen. The applicant has observed that BHNE cells cultured on impermeable substrates 22 are predominantly squamous in shape and tend to have shorter microvilli and almost no cilia. Such cells are, however, useful for patch clamp studies and the like.

Figure 6:
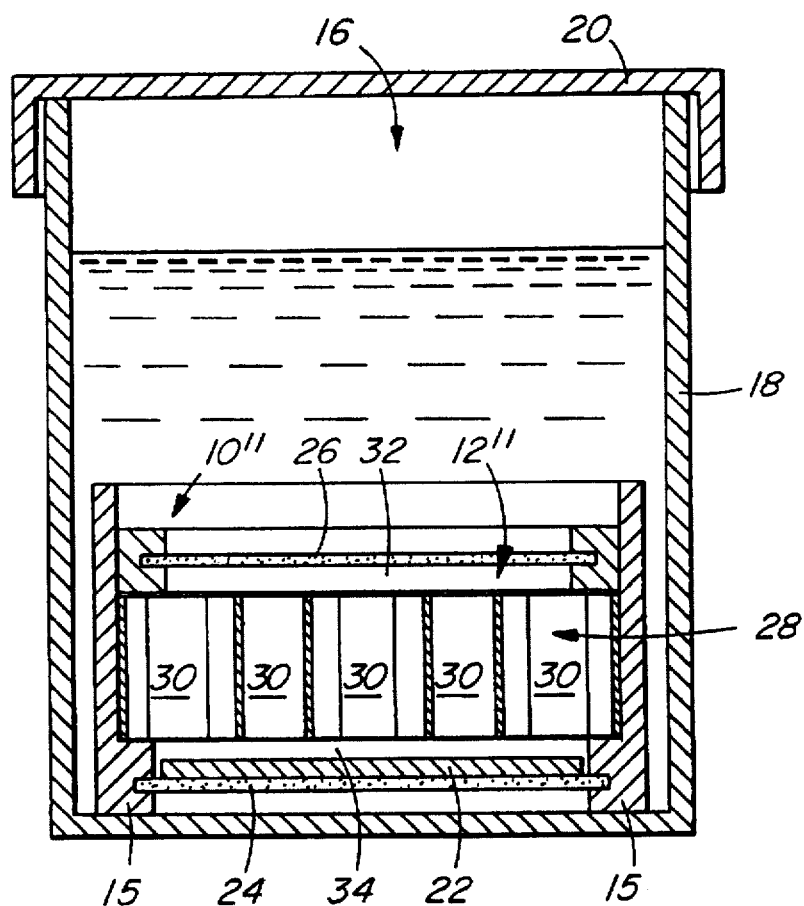
FIG. 6 is a sectional view of a further alternative culture dish insert.

FIG. 6 illustrates a further alternative culture dish insert $10^{11}$ for culturing BHNE cells on either permeable or impermeable substrates in accordance with the applicant's method. As in the FIG. 3 and 5 embodiments, insert $10^{11}$ is positionable with one reservoir 16 formed in a sterile culture dish 18 having a lid 20.

Insert $10^{11}$ defines a reservoir $12^{11}$ which is separated from reservoir 16 by a fluid permeable first baffle 26. Baffle 26 is relatively thin and is supported by a second baffle 28 placed within insert $10^{11}$, as shown in FIG. 6 and described further below. As in the FIG. 5 embodiment, the bottom surface of reservoir $12^{11}$ consists of a fluid impermeable substrate 22 coated with an adherence surface. Substrate 22 is supported on a fluid permeable membrane 24. Alternatively, substrate 22 and membrane 24 could be replaced with a fluid permeable adherence substrate, such as collagen derived from bovine chorionic tissue or the like. Insert $10^{11}$ also includes a plurality of foot supports 15 for elevating impermeable substrate 22 and membrane 24 above the bottom of dish 18.

Figure 7:
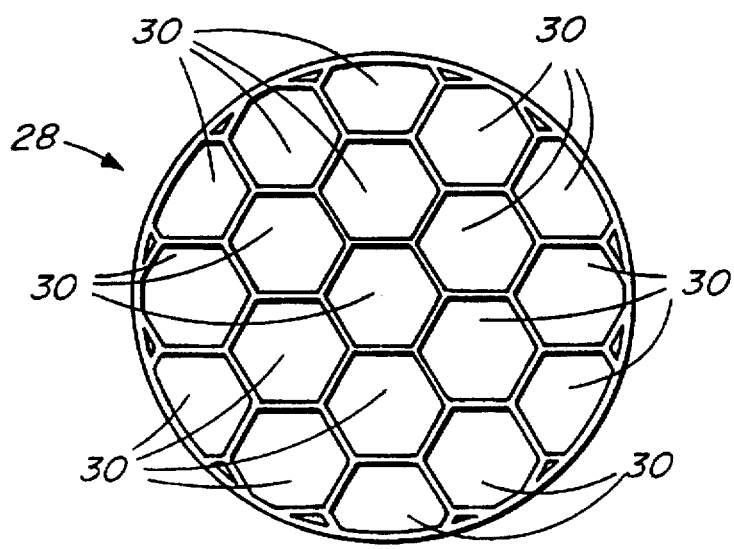
FIG. 7 is a top plan view of a baffle forming part of the insert of FIG. 6.

Second fluid permeable baffle 28 is insertable within reservoir $12^{11}$ between substrate 22 and first baffle 26. As shown in FIG. 6, second baffle 28, which is relatively thick in comparison to baffle 26, is supported on a ledge projecting inwardly from the sidewalls of insert $10^{11}$ at a position elevated above adherence substrate 22. With reference to FIG. 7, second baffle 28 preferably comprises a plurality of honeycomb-like compartments 30 open at their upper and lower ends. Culture medium can thus flow freely through baffle compartments 30 between an upper portion 32 of reservoir $12^{11}$ adjacent first baffle 26 and a lower portion 34 of reservoir $12^{11}$ adjacent adherence substrate 22. As discussed further below, the purpose of second baffle 28 is to lessen the flow of fluid medium and suspended cells within reservoir $12^{11}$.

In use, the harvested BHNE cells are suspended in the fluid culture medium and introduced into lower portion 34 of insert reservoir $12^{11}$. Second baffle 28 is then inserted into reservoir $12^{11}$ and insert $10^{11}$ is filled with fluid culture medium to a level approximately 1 mm above the top of second baffle 28. First baffle 26 is then positioned on top of baffle 28. The next step in the procedure is to puncture the membrane of first baffle 26 using a sterile tuberculin syringe and aspirate trapped air bubbles. After withdrawing the syringe, reservoir 16 is filled with fluid culture medium to a level above the level of first baffle 26 (FIG. 6). Preferably the total depth of culture medium in reservoirs 16 and $12^{11}$ is approximately 24 mm.

In accordance with the applicant's method, culture medium is periodically replenished by aspirating medium from reservoir 16 and replacing it with fresh medium. The fresh medium diffuses across first baffle 26 into reservoir $12^{11}$. The fresh medium can freely pass through baffle compartments 30 to feed the BHNE cells which are typically located in the lower portion 34 of reservoir $12^{11}$ on or near adherence substrate 22.

Baffle 28 is provided for minimizing the disturbance to the BHNE cells within insert $10^{11}$, such as would occur when the culture dish 18 is moved from one location to another. In particular, baffle 28 restricts the circulation of fluid within reservoir $12^{11}$ to ensure that weak cell-cell and cell-substrate adherence are not disrupted when insert $10^{11}$ is handled as aforesaid.

As should be apparent to someone skilled in the art, the vertical sidewalls of insert $10^{11}$ could be extended upwardly to define a reservoir 16 directly above first baffle 26, provided that adherence substrate 22 and membrane 24 are fluid impermeable. In this embodiment it would not be necessary to place insert $10^{11}$ in a separate culture dish 18. Rather, a removable cover 20 could be provided for placement directly on insert $10^{11}$. This alternative embodiment would only be suitable for culturing cells on impermeable substrates 22.

The applicant's cell culture method described herein has proven successful in culturing human bronchial epithelial cells in addition to BHNE cells. Experiments involving respiratory cells harvested from non-human donors have also proven successful. For example, brushed goat nasal epithelial cells can be readily cultured on CELLAGEN™ inserts 10 such as illustrated in FIGS. 2 and 3. One cell culture medium which has proven to be effective in the culture of goat nasal epithelial cells is bronchial epithelial growth medium (BEGM) referred to above supplemented with 1% (v/v) FBS.

As it should be apparent to someone skilled in the art, the applicant's cell culture protocol and culture dish design shown in FIG. 6 may also prove useful in culturing non-epithelial cells and cells harvested from donor organisms using more invasive procedures. The important advantage of the applicant's culture dish insert $10^{11}$ is that it affords the ability to periodically renew the culture medium while preventing the loss of the cell inoculum. The more cells in the inoculum that contribute to the seeding of the adherence substrate to achieve a given degree of confluence, the less cell replication will be required (to create daughter cells to reach that level of confluence) and, therefore, less phenotypic and genotypic drift will be exhibited by the final cultured product. Accordingly, the cultured cells should be more native and homogeneous, assuming the initial cell inoculum is homogeneous.

Respiratory and non-respiratory epithelial cells could be harvested using more invasive techniques, such as surgical biopsy, from a wide variety of tissues including airway structures (e.g. sinuses, tracheae, bronchi, bronchioles), gastrointestinal tract (e.g. esophagus, stomach, small and large intestine and the ducts of accessory glands such as salivary glands, gallbladder, liver and pancreas), urinary tract, genital tract, integument, endothelium, and mesothelium. Further, cells and cell clusters harvested from any epithelial compartment using a brush (or curette) to remove cells as sheets or clusters may also be culturable using the method and novel culture dish described herein.

Other possible applications for the applicant's new culture dish could be to re-start the culture of cryopreserved cells and to initiate cultures from explanted tissues.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A method of culturing in vitro non-transformed epithelial cells obtained from the respiratory tract mucosa of a mammalian donor, said method, comprising:
    (a) harvesting said epithelial cells from said mucosa by brushing or scraping said cells from underlying tissue;
    (b) suspending said epithelial cells in a fluid culture medium to form a cell suspension;
    (c) introducing said cell suspension into a first reservoir having a bottom surface comprising an adherence substrate;
    (d) introducing additional fluid culture medium into a second reservoir separated from said first reservoir by a fluid permeable baffle;
    (e) incubating said cells under conditions suitable for promoting epithelial cell growth for a period of at least 72 hours without removing non-adherent cellular material from said first reservoir; and
    (f) changing said fluid culture medium within said second reservoir during said incubation period at intervals of approximately 24–72 hours without disturbing said epithelial cells within said first reservoir, including said non-adherent cellular material.

2. The cell culture method as defined in claim 1, wherein said incubation step is continued until said epithelial cells form a confluent layer on said adherence substrate.

3. The cell culture method as defined in claim 1, wherein said incubation step is continued until greater than about 25% of said epithelial cells adhere, flatten and begin to replicate on said adherence substrate.

4. The cell culture method as defined in claim 1, wherein some of said epithelial cells within said cell suspension are aggregates of initially non-adherent cells, and wherein said incubation step is continued until the majority of said initially non-adherent cells adhere, flatten and begin to replicate on said adherence substrate.

5. The cell culture method as defined in claim 1, wherein said epithelial cells are incubated at 37° C. and 5% $CO_2$.

6. The cell culture method as defined in claim 1, wherein said baffle comprises said adherence substrate.

7. The cell culture method as defined in claim 6, wherein said adherence substrate comprises an upper surface exposed to said first reservoir and a lower surface exposed to said second reservoir.

8. The cell culture method as defined in claim 6, herein said adherence substrate is a collagen matrix.

9. The cell culture method as defined in claim 8, wherein said collagen matrix is made from collagen extracted from bovine chorion.

10. The cell culture method as defined in claim 1 wherein said adherence substrate is located on said fluid permeable baffle.

11. The cell culture method as defined in claim 10, wherein said adherence substrate is fluid impermeable and wherein said adherence substrate covers only a portion of said fluid permeable baffle.

12. The cell culture method as defined in claim 11, wherein said adherence substrate is a glass coverslip coated with an adherence surface.

13. The cell culture method as defined in claim 1, wherein said fluid culture medium comprises Ham's F12 medium supplemented with growth factors selected from the group consisting of insulin, hydrocortisone, tri-iodothyronine, endothelial cell growth supplement, epidermal growth factor and cholera toxin.

14. The cell culture method as defined in claim 1, further comprising the step of introducing a fluid culture medium supplement comprising epithelial cell proliferation activators into said second reservoir during said incubation step.

15. The cell culture method as defined in claim 14, wherein said supplement comprises modified LHC9 medium.

16. The cell culture method as defined in claim 14, wherein said supplement comprises bronchial epithelial growth medium (BEGM).

17. The cell culture method as defined in claim 2, further comprising the steps of:
  (a) dissociating said confluent layer of epithelial cells from said adherence substrate by enzymatic treatment; and
  (b) amplifying said dissociated epithelial cells by serial subcultivation techniques.

18. The cell culture method as defined in claim 1, wherein said epithelial cells are introduced into said first reservoir less than 1 hour following harvesting of said cells from said donor.

19. The cell culture method as defined in claim 1, further comprising the step of treating said cells with fetal bovine serum prior to introducing said cells into said first reservoir.

20. A method of culturing non-transformed mammalian respiratory epithelial cells in vitro, comprising:
  (a) harvesting said epithelial cells from the respiratory tract of a mammalian donor by brushing or scraping;
  (b) suspending said epithelial cells in a fluid culture medium to form a cell suspension;
  (c) introducing said cell suspension into a first reservoir having a bottom surface comprising a fluid permeable adherence substrate;
  (d) introducing additional fluid culture medium into a second reservoir separated from said first reservoir by said adherence substrate;
  (e) incubating said cells under conditions suitable for promoting epithelial cell growth until said epithelial cells form a confluent layer on said adherence substrate without removing non-adherent cellular material within said first reservoir; and
  (f) changing said fluid culture medium within said second reservoir during said incubation period at intervals of approximately 24–72 hours without disturbing said epithelial cells within said first reservoir, including said non-adherent cellular material.

* * * * *